US010709601B2

(12) United States Patent
Adair (10) Patent No.: US 10,709,601 B2
(45) Date of Patent: Jul. 14, 2020

(54) PERSONAL COOLING AND HEATING DEVICE

(71) Applicant: John Adair, Reynoldsburg, OH (US)

(72) Inventor: John Adair, Reynoldsburg, OH (US)

( * ) Notice: Subject to any disclaimer, the term of this patent is extended or adjusted under 35 U.S.C. 154(b) by 326 days.

(21) Appl. No.: 15/696,103

(22) Filed: Sep. 5, 2017

(65) Prior Publication Data

US 2018/0064574 A1 Mar. 8, 2018

Related U.S. Application Data

(60) Provisional application No. 62/383,194, filed on Sep. 2, 2016.

(51) Int. Cl.
*A61F 7/00* (2006.01)
*A61F 7/02* (2006.01)

(52) U.S. Cl.
CPC .............. *A61F 7/007* (2013.01); *A61F 7/02* (2013.01); *A61F 2007/0011* (2013.01); *A61F 2007/0055* (2013.01); *A61F 2007/0057* (2013.01); *A61F 2007/0075* (2013.01)

(58) Field of Classification Search
CPC ................. A61F 2007/0011; A61F 2007/0075
See application file for complete search history.

(56) References Cited

U.S. PATENT DOCUMENTS

| 4,190,054 A | 5/1980 | Brennan |
| 4,470,263 A * | 9/1984 | Lehovec ............ A41D 13/0053 62/259.3 |
| 4,576,169 A | 3/1986 | Williams |
| 4,741,338 A * | 5/1988 | Miyamae ................. A61F 7/00 607/112 |
| 4,745,922 A | 5/1988 | Taylor |
| D298,458 S | 11/1988 | Margolin et al. |
| 4,905,475 A | 3/1990 | Tuomi |
| 4,930,317 A | 6/1990 | Klein |
| 4,962,761 A * | 10/1990 | Golden ................ A61F 7/02 165/46 |
| 5,088,549 A | 2/1992 | Schneider |
| 5,146,765 A | 9/1992 | Waters |
| 5,211,623 A | 5/1993 | Sarkozi |
| 5,295,949 A | 3/1994 | Hathaway |
| 5,802,865 A | 9/1998 | Strauss |
| 6,125,636 A | 10/2000 | Taylor et al. |
| 6,189,327 B1 | 2/2001 | Srauss et al. |

(Continued)

*Primary Examiner* — Kaitlyn E Smith
(74) *Attorney, Agent, or Firm* — Porter, Wright, Morris & Arthur, LLP (57) ABSTRACT

A temperature regulating device for a user's neck includes a housing that extends about the neck and has a base portion, and first and second side portions. The side portions each have an air duct extending from an air inlet to an air outlet in communication with air inlets of an air duct within the base portion. Two thermoelectric are devices located within each of the side portions. Each thermoelectric device is in thermal connection with a cold space member at exterior sides of the side portions for contacting the lateral sides of the neck. Two fans within the base portion are configured to pull air through the side portions past the thermoelectric devices to the base portion and out through the air outlets of the base portion. Only the side portions of the housing selectively heat and cool the neck near pulse points of the neck.

18 Claims, 11 Drawing Sheets

(56) References Cited

U.S. PATENT DOCUMENTS

| | | |
|---|---|---|
| D442,269 S | 5/2001 | Pinchuk |
| D455,481 S | 4/2002 | Christianson |
| D457,945 S | 5/2002 | Pinchuk |
| 6,942,015 B1 | 9/2005 | Jenkins |
| 7,043,765 B1 | 5/2006 | Otsubo |
| 7,296,304 B2 * | 11/2007 | Goldsborough ....... A42B 3/285 2/171.3 |
| 7,721,349 B1 | 5/2010 | Strauss |
| D676,139 S | 2/2013 | Golzari |
| 8,397,518 B1 | 3/2013 | Vistakula |
| 9,089,411 B2 | 7/2015 | Sandhu et al. |
| D738,995 S | 9/2015 | Shapiro et al. |
| D747,810 S | 1/2016 | Bangser et al. |
| D777,890 S | 1/2017 | Hsiao et al. |
| D780,899 S | 3/2017 | Hsiao et al. |
| 9,622,519 B2 | 4/2017 | Hsiao et al. |
| 2002/0103520 A1 | 8/2002 | Latham |
| 2004/0211189 A1 | 10/2004 | Arnold |
| 2005/0149153 A1 | 7/2005 | Nakase |
| 2005/0177925 A1 | 8/2005 | Peeples |
| 2007/0193278 A1 | 8/2007 | Polacek et al. |
| 2007/0213794 A1 | 9/2007 | Lauver |
| 2008/0015665 A1 * | 1/2008 | Lachenbruch ............ A61F 7/10 607/104 |
| 2008/0122275 A1 | 5/2008 | Flory et al. |
| 2010/0050658 A1 | 3/2010 | Ali |
| 2010/0185267 A1 * | 7/2010 | Dickie ...................... A61F 7/10 607/109 |
| 2010/0198322 A1 | 8/2010 | Joseph et al. |
| 2010/0198323 A1 | 8/2010 | Jung |
| 2011/0259028 A1 | 10/2011 | Lee |
| 2011/0299027 A1 | 12/2011 | Shantha et al. |
| 2013/0085552 A1 | 4/2013 | Mandel |
| 2015/0223973 A1 | 8/2015 | Frederick |
| 2015/0238349 A1 | 8/2015 | Giuliani |
| 2015/0374045 A1 | 12/2015 | Codner |
| 2016/0058134 A1 | 3/2016 | Blunt |
| 2017/0035602 A1 * | 2/2017 | Shapiro ................... A61F 7/007 |
| 2017/0209301 A1 * | 7/2017 | Deseve ................... A61F 7/007 |

* cited by examiner

PERSONAL COOLING AND HEATING DEVICE

CROSS-REFERENCE TO RELATED APPLICATIONS

This application claims the priority benefit of U.S. Provisional Patent Application No. 62/383,194 filed on Sep. 2, 2016, the disclosure of which is expressly incorporated herein in its entirety by reference.

STATEMENT REGARDING FEDERALLY SPONSORED RESEARCH

Not applicable

PARTIES TO A JOINT RESEARCH AGREEMENT

Not Applicable

REFERENCE TO APPENDIX

Not applicable

FIELD OF THE INVENTION

The field of the present invention relates to personal temperature regulating devices, and more particularly, to such devices that can be worn about a body portion of a user to cool and/or heat the user.

BACKGROUND OF THE INVENTION

The core body temperature of the average adult human is normally about 98.6° Fahrenheit (about 37.0° Celsius). However, body temperatures vary depending on certain conditions such as physical activity, environment etc. Humans have trouble adapting to extreme temperature conditions.

If you're partaking in physically exerting activities in a hot environment, or even just exposed to a hot environment for a prolonged period of time, your body temperature could rise to dangerous levels. If your body temperature reaches about 104° Fahrenheit (about 40° Celsius), you could experience heatstroke. Lowering your body core temperature for short periods of time can help you avoid heatstroke, improve sleep, or reduce a fever, but it's important to do so safely so that your body temperature is not reduced too much.

If you are exposed to a cold environment for a prolonged period of time, your body temperature could lower to dangerous levels. It's important that you conserve body heat and raise your core temperature to avoid organ failure and even death due to prolonged low body temperature. Only a three degree reduction in body temperature (about 95° F. (about 35° C.)) is needed to induce hypothermia. Raising your body core temperature for short periods of time can help you avoid hypothermia but it's important to do so safely so that your body temperature is not increased too much.

Change in body temperatures can also exacerbate medical conditions of existing patients. For example, a temperature increase can make many people with multiple sclerosis (MS) experience a temporary worsening of their symptoms. Doctors believe that this occurs because heat causes nerves (whose myelin covering has been destroyed from MS) to conduct electrical signals even less efficiently. Additionally, for reasons that are not well understood, decreases in body temperature can also cause MS symptoms, usually spasticity, to flare.

Attempts have been made to provide personal cooling devices. For example see U.S. Pat. Nos. 5,802,865 and 6,189,327, the disclosures of which are incorporated herein in there entireties by reference. These personal cooling devices are evaporative type devices that fit around a person's neck or head. Body heat is transferred away by a fan-induced flow of moistened air. While such prior devices may provide the user with some perception of cooling, they are ineffective at rapidly reducing the user's core body temperature and cannot lower temperature below room temperature. Additionally, these prior devices require the user to replenish a water supply which can be difficult or even impossible under some conditions.

Other attempts to provide a personal cooling or heating device utilize Peltier thermoelectric devices. For example see U.S. Pat. No. 6,125,636, the disclosure of which is incorporated herein in its entirety by reference. While such prior devices actively cool to provide the user with perception of rapid cooling or heating, these prior devices are designed to concentrate cooling the forehead or back of the neck. The area of the brain that senses and regulates body temperature is located in the base of the neck in an area of the brain called the brainstem. Cooling this spot down tricks the body into feeling like it is cooler than it really is. Thus, the process of cooling or heat may be stopped prior to adequately lowering or raising the user's body temperature. Additionally, using such inefficient cooling or heating spots on the body takes an undesirable amount of time to adequately lower or raise the user's body temperature.

Accordingly, there exists a need for a personal cooling and/or heating device that effectively and rapidly lowers and/or raises the user's body temperature.

SUMMARY OF THE INVENTION

The present invention provides personal temperature regulating devices which address at least one of the above-noted problems of the prior art. Disclosed herein is a body temperature regulating device for use on a body portion of a user. The temperature regulating device comprises a housing configured to extend partially about the body portion and having a base portion, first side portion extending from a first end of the base portion, and second side portion extending from a second end of the base portion opposite the first end. The base portion has an interior air duct with a first air inlet, a second air inlet, and at least one air outlet. The first side portion has a distal end opposite the base portion, a proximal end at the base portion, and an interior air duct extending from an air inlet at the distal end to an air outlet at the proximal end in communication with the first air inlet of the interior air duct of the base portion. The second side portion has a distal end opposite the base portion, a proximal end at the base portion, and an interior air duct extending from an air inlet at the distal end to an air outlet at the proximal end in communication with the second air inlet of the interior air duct of the base portion. At least one thermoelectric device is located within the first side portion and having a first side in thermal connection with a cold space member at least partially forming an exterior side of the first side portion and a second side in thermal connection with a heat sink located within the air duct of the first member. At least one thermoelectric device located within the second side portion and having a first side in thermal connection with a cold space member at least partially forming an exterior side of the second side portion and a second side in thermal connection with a heat sink located within the air duct of the second side portion. At least one fan is within the air duct of the base portion at the at least one air outlet of the base portion and configured to pull air into at least one of the air inlets of the first and second side portions and out through the at least one air outlet of the base portion.

Also disclosed herein is a body temperature regulating device for use on a body portion of a user comprises a housing configured to extend partially about the body portion and having a base portion, first side portion extending from a first end of the base portion, and second side portion extending from a second end of the base portion opposite the first end. First and second thermoelectric device are located within the first side portion and having a first side in thermal connection with a first cold space member at least partially forming an exterior side of the first side portion and a second side in thermal connection with a heat sink located within an air duct of the first member. First and second thermoelectric devices are also each located within the second side portion and having a first side in thermal connection with a second cold space member at least partially forming an exterior side of the second side portion and a second side in thermal connection with a heat sink located within the air duct of the second side portion.

Also disclosed herein is a body temperature regulating device for use on a neck of a user that comprises a housing configured to extend partially about the neck of the user and having a base portion, first side portion extending from a first end of the base portion, and second side portion extending from a second end of the base portion opposite the first end. The base portion has an interior air duct with a first air inlet, a second air inlet, a first air outlet, and a second air outlet. The first side portion has a distal end opposite the base portion, a proximal end at the base portion, and an interior air duct extending from an air inlet at the distal end to an air outlet at the proximal end in communication with the first air inlet of the interior air duct of the base portion. The second side portion has a distal end opposite the base portion, a proximal end at the base portion, and an interior air duct extending from an air inlet at the distal end to an air outlet at the proximal end in communication with the second air inlet of the interior air duct of the base portion. Two thermoelectric devices are located within the first side portion and each having a first side in thermal connection with a cold space member at least partially forming an exterior side of the first side portion and a second side in thermal connection with a heat sink located within the air duct of the first member. Two thermoelectric devices are located within the second side portion and each having a first side in thermal connection with a cold space member at least partially forming an exterior side of the second side portion and a second side in thermal connection with a heat sink located within the air duct of the second side portion. A first fan within the air duct of the base portion at first air outlet of the base portion and configured to pull air into at least one of the air inlets of the first and second side portions and out through the first air outlet of the base portion. A second fan is within the air duct of the base portion at the second air outlet of the base portion and configured to pull air into at least one of the air inlets of the first and second side portions and out through the second air outlet of the base portion.

From the foregoing disclosure and the following more detailed description of various preferred embodiments it will be apparent to those skilled in the art that the present invention provides a significant advance in the technology and art of personal cooling and/or heating device. Particularly, significant in this regard is the potential the invention affords for providing a reliable and effective self-contained personal temperature regulating device that rapidly lowers and raises the user's core body temperature without adverse impact by the surrounding environment. Additional features and advantages of the invention will be better understood in view of the detailed description provided below.

BRIEF DESCRIPTION OF THE DRAWINGS

These and further objects of the invention will become apparent from the following detailed description.

Figure 1:
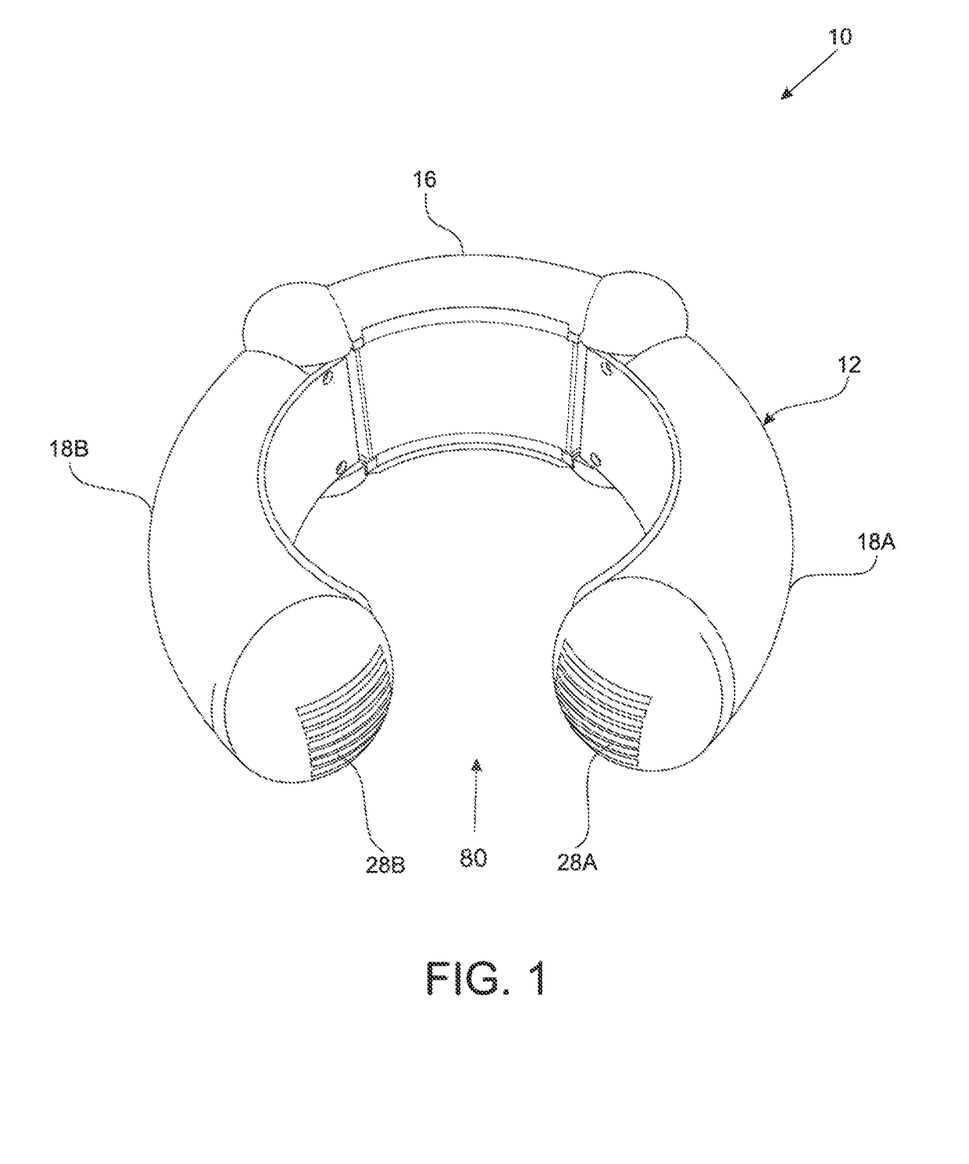
FIG. 1 is a font perspective view of a personal temperature regulating device according to the present invention.
Figure 2:
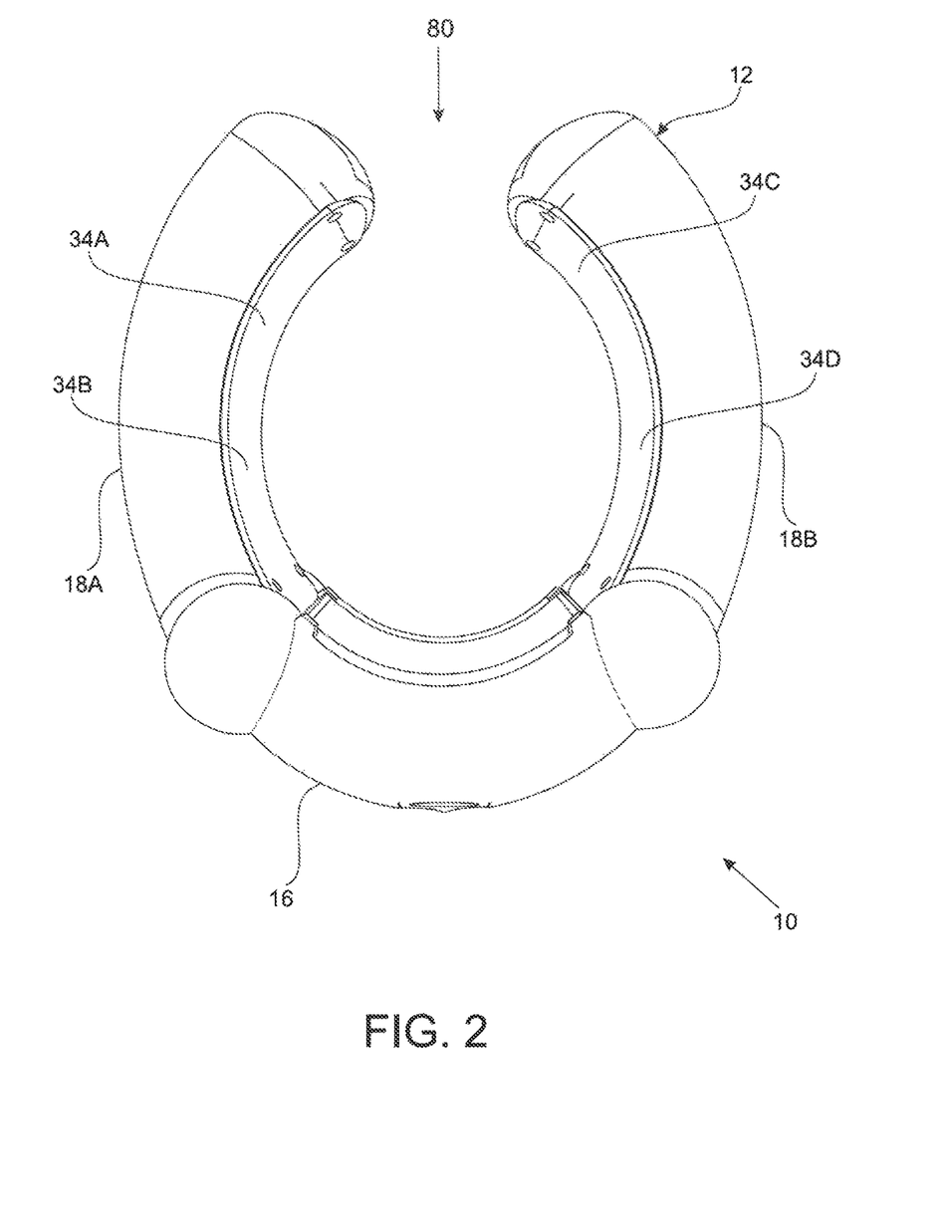
FIG. 2 is a top plan view of the personal temperature regulating device of FIG. 1, wherein the bottom plan view id the same.
Figure 3:
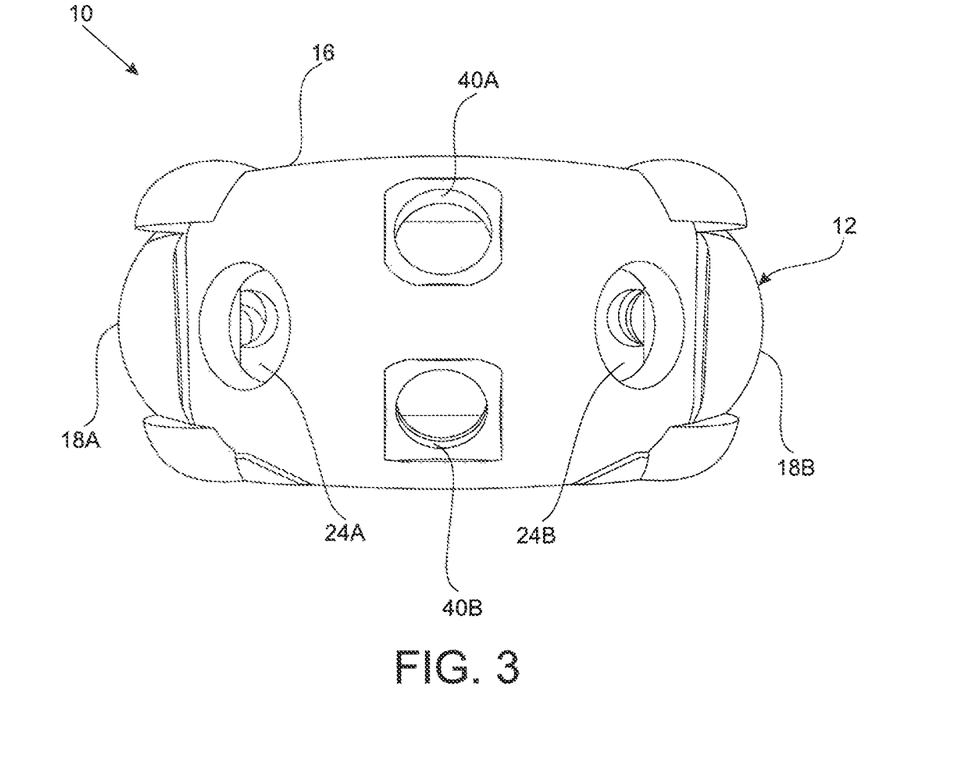
FIG. 3 is a rear elevational view of personal temperature regulating device of FIGS. 1 and 2, wherein some items are removed for clarity.
Figure 4:
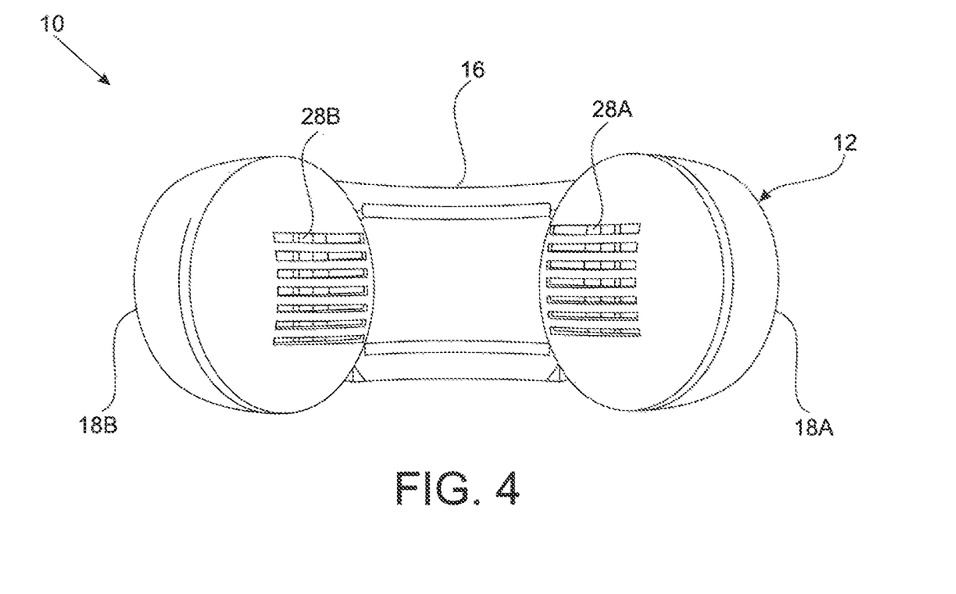
FIG. 4 is a front elevational view of personal temperature regulating device of FIGS. 1 to 3.
Figure 5:
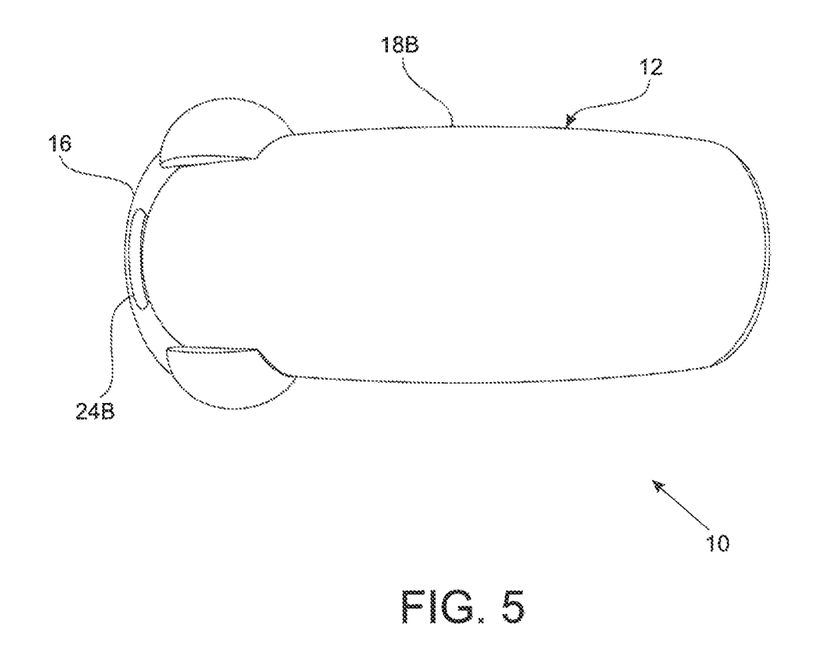
FIG. 5 is a right-side elevational view of the personal temperature regulating device of FIGS. 1 to 4.
Figure 6:
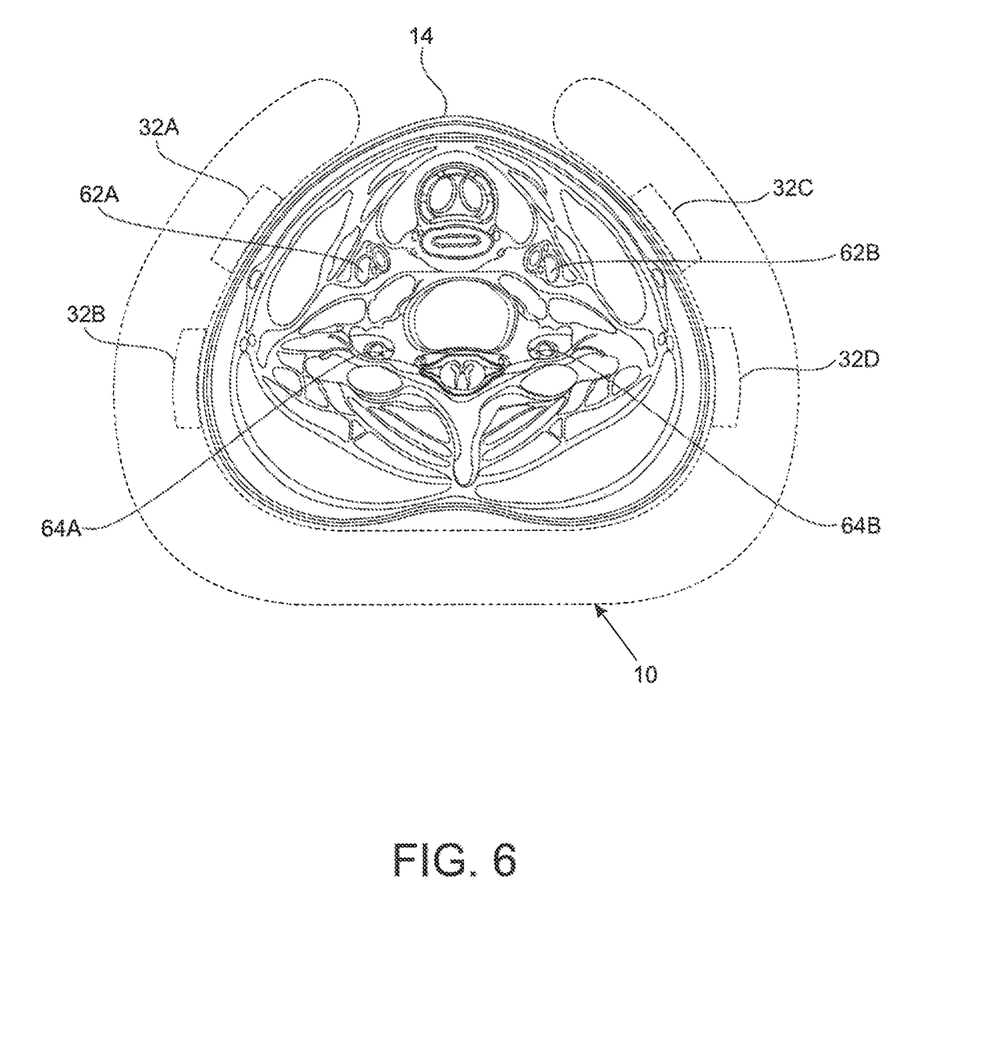
FIG. 6 is a diagrammatic view of the personal temperature regulating device of FIGS. 1 to 5 placed about the neck of a user.
Figure 7:
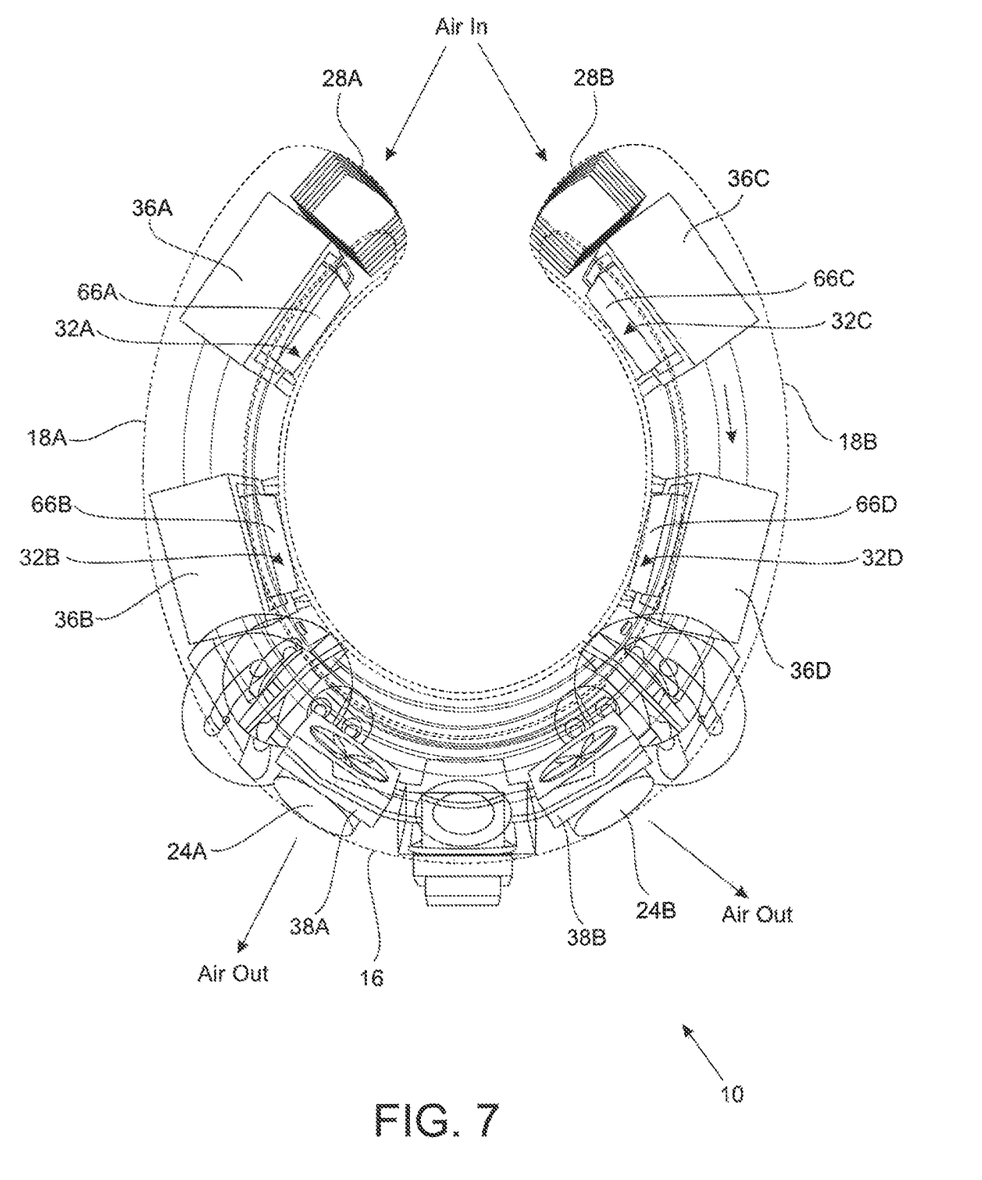
FIG. 7 is a top plan view of the personal temperature regulating device of FIGS. 1 to 6 similar to FIG. 3 but wherein certain components are illustrated as transparent to show internal components.

It should be understood that the appended drawings are not necessarily to scale, presenting a somewhat simplified representation of various preferred features illustrative of the basic principles of the invention. The specific design features of the various personal temperature regulating devices as disclosed herein, including, for example, specific dimensions, orientations, locations, and shapes will be determined in part by the particular intended application and use environment. Certain features of the illustrated embodiments have been enlarged or distorted relative to others to facilitate visualization and clear understanding. In particular, thin features may be thickened, for example, for clarity or illustration. All references to direction and position, unless otherwise indicated, refer to the orientation of the personal temperature regulating device illustrated in the drawings. In general, up or upward generally refers to an upward direction out of the plane of the paper in FIG. 2 and down or downward generally refers to a downward direction into the plane of the paper in FIG. 2. Also in general, fore or forward generally refers to an upward direction within the plane of the paper in FIG. 2 and aft or rearward generally refers to a downward direction within the plane of the paper in FIG. 2.

DETAILED DESCRIPTION OF CERTAIN PREFERRED EMBODIMENTS

It will be apparent to those skilled in the art, that is, to those who have knowledge or experience in this area of technology, that many uses and design variations are possible for the personal temperature regulating devices disclosed herein. The following detailed discussion of various alternative and preferred embodiments will illustrate the general principles of the invention with regard to the specific application of personal temperature regulating devices configured for cooling and/or heating the pulse points (where an artery is close to the surface of the skin) in the neck of a human user. Other embodiments suitable for other applications will be apparent to those skilled in the art given the benefit of this disclosure such as, for example, personal temperature regulating devices configured for cooling and/or heating the pulse points (where an artery is close to the surface of the skin) in the wrist, the inner thigh, the inside of elbows, the inside of knees, and/or the top of feet of a human user.

FIGS. 1 to 8 illustrate a personal temperature regulating device 10 according to the present invention. The illustrated personal temperature regulating device 10 includes a housing 12 configured to extend partially about the body portion 14 (in this embodiment a neck) and having a base portion 16, first or left side portion 18A extending from a first or left end of the base portion 16, and a second or right side portion 18B extending from a second or right end of the base portion 16 opposite the first end. The base portion 16 has an interior air duct 20 with a first air inlet 22A, a second air inlet 22B, and at least one air outlet 24A, 24B. The first side portion 18A has a distal end opposite the base portion 16, a proximal end at the base portion 16, and an interior air duct 26 extending from an air inlet 28A at the distal end to an air outlet 30A at the proximal end in communication with the first air inlet 22A of the interior air duct 20 of the base portion 16. The second side portion 18B has a distal end opposite the base portion 16, a proximal end at the base portion 16, and an interior air duct 26 extending from an air inlet 28B at the distal end to an air outlet 28B at the proximal end in communication with the second air inlet 22B of the interior air duct 20 of the base portion 16. At least one thermoelectric device 32A, 32B is located within the first side portion 18A and having a first side in thermal connection with a cold space member 34A, 34B at least partially forming an exterior side of the first side portion 18A and a second side in thermal connection with a heat sink 36A, 36B located within the air duct 26 of the first side portion 18A. At least one thermoelectric device 32C, 34D located within the second side portion 18B and having a first side in thermal connection with a cold space member 34C, 34D at least partially forming an exterior side of the second side portion 18B and a second side in thermal connection with a heat sink 36C, 36D located within the air duct 26 of the second side portion 18B. At least one electric fan 38A, 38B is located within the air duct 20 of the base portion 16 at the at least one air outlet 24A, 24B of the base portion 16 and configured to pull air into at least one of the air inlets 28A, 28B of the first and second side portions 18A, 18B and out through the at least one air outlet 24A, 24B of the base portion 16.

Figure 8:
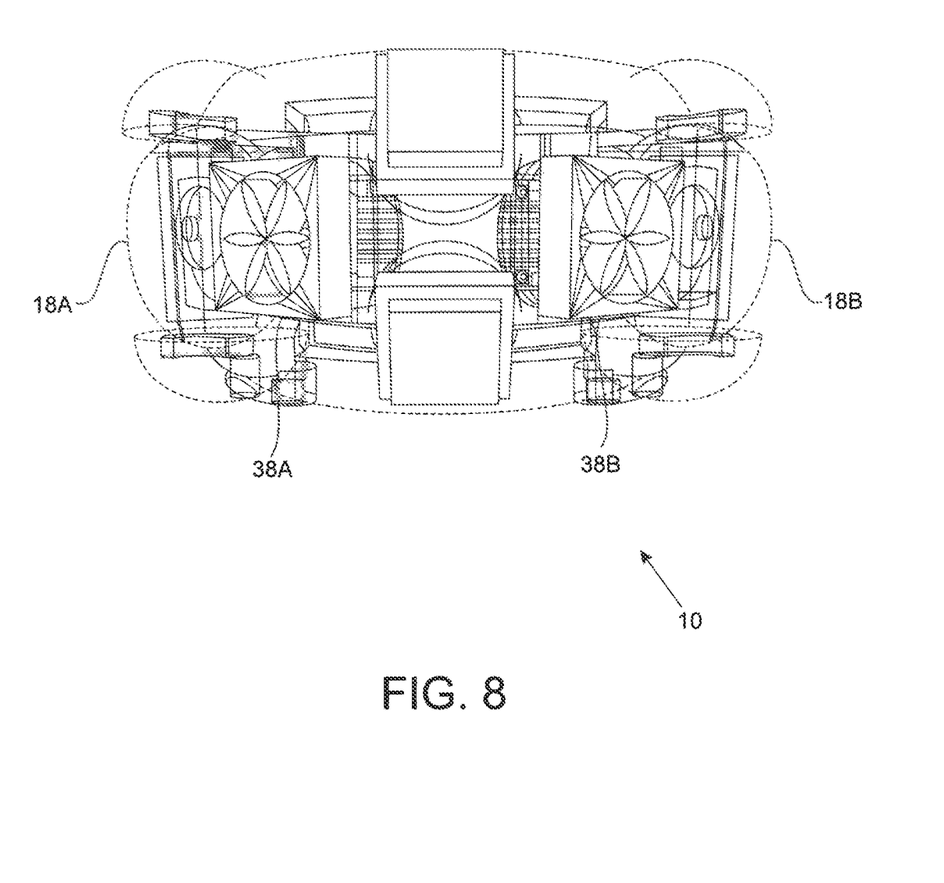
FIG. 8 is a rear elevational view of the personal temperature regulating device of FIGS. 1 to 7 similar to FIG. 4 but wherein certain components are illustrated as transparent to show internal components.
Figure 9:
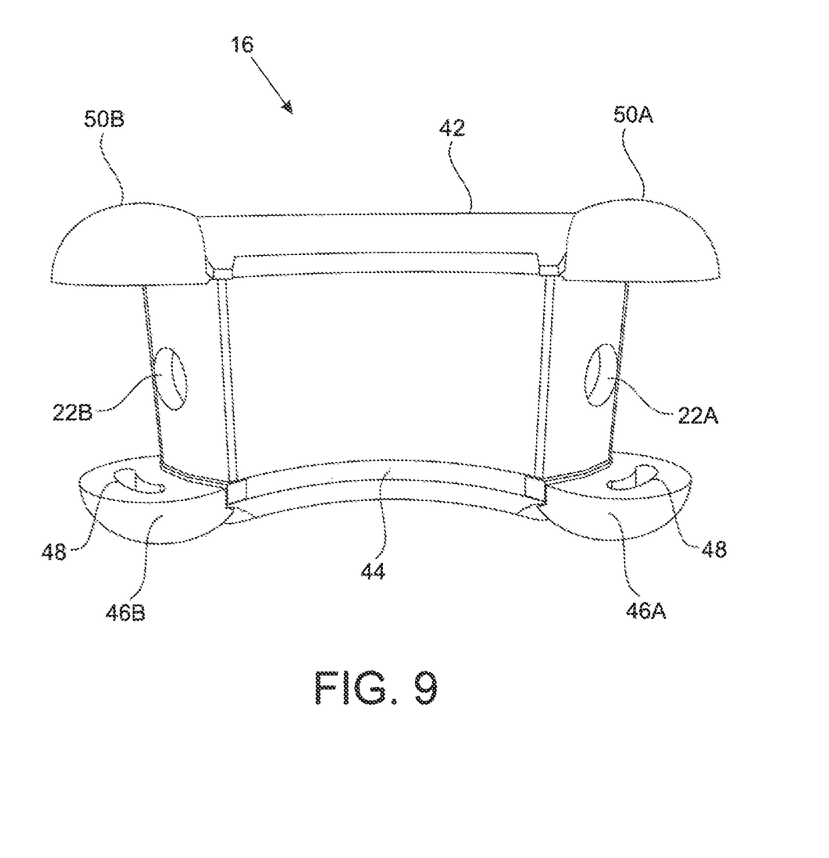
FIG. 9 is a front elevational view of a rear member of the personal temperature regulating device of FIGS. 1 to 8.
Figure 10:
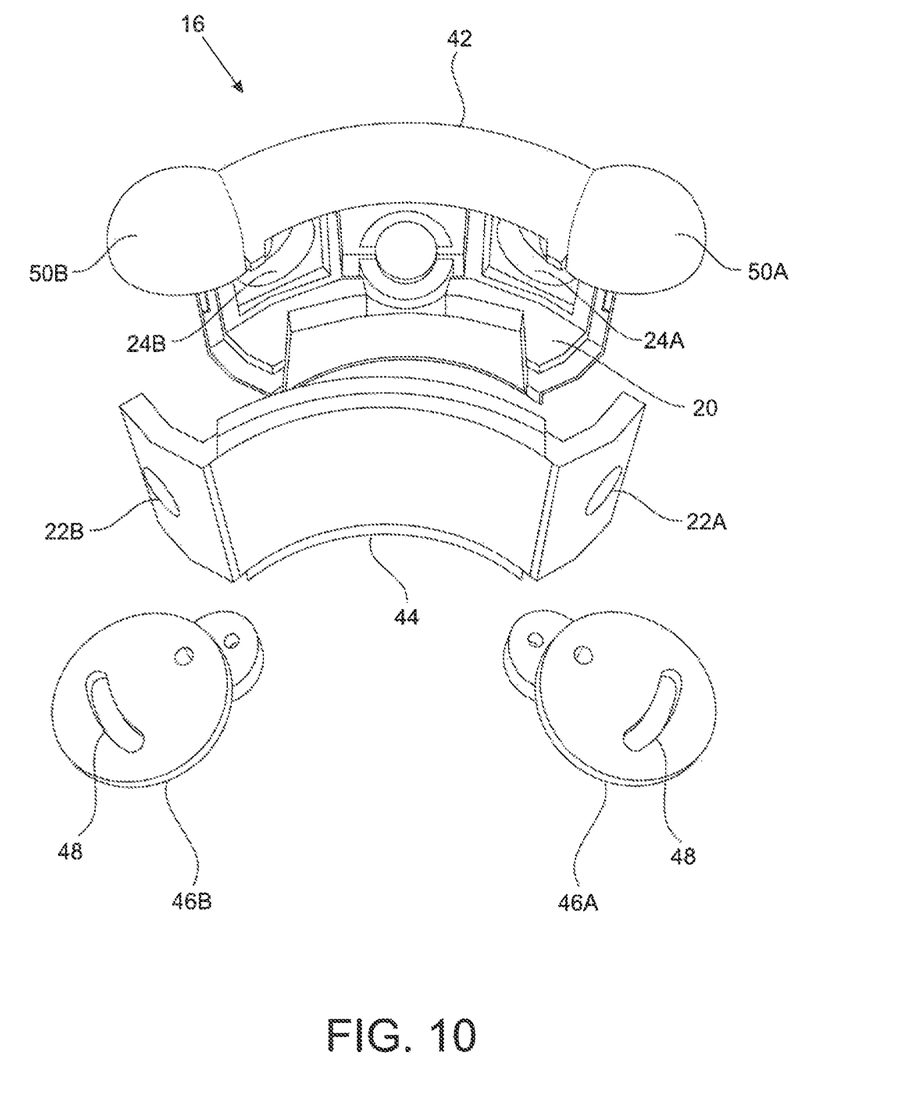
FIG. 10 is an exploded view of the rear member of FIG. 9.

As best shown in FIGS. 8 and 9 the illustrated base portion 16 of the housing 12 is generally arcuate shaped so that it extends about the rear or base portion of the user's neck 14. The base portion 16 forms the hollow interior space or air duct 20. The illustrated air duct 20 has an air inlet 22A, 22B at each end of the base portion 16. Each of the air inlets 22A, 22B is associated with one of the two side portions 18A, 18B as is described in more detail hereinbelow. The illustrated air inlets 22A, 22B are circular openings extending through the wall but any other suitable configuration can be utilized. The illustrated air duct 20 also has a pair of laterally spaced-apart air outlets 24A, 24B in the rear side of the base portion 16. Each of the air outlets 24A, 24B is associated with one of the electric fans 38A, 38B as described in more detail below. The illustrated air outlets 24A, 24B are circular openings extending through the wall but any other suitable configuration can be utilized. The illustrated base portion 16 is also provided with a pair of vertically spaced-apart switch openings 40A, 40B in the rear side of the base portion 16 between the air outlets 24A, 24B. Each of the switch openings 40A, 40B is associated with a control switch as described in more detail below. The illustrated switch openings 40A, 40B are circular openings extending through the wall but any other suitable configuration can be utilized.

The illustrated base portion 16 includes a body member 42 that primarily forms the top, bottom and rear walls of the base portion 16, a cover member 44 that primarily forms the front and end walls of the base portion 16, and a pair of lower joint members 46A, 46B that partially form joints with the side portions 18A, 18B respectively. The illustrated cover member 44 is removably secured to the body member 42 in any suitable manner for assembly and repair of components located within the base portion 16 of the housing 12. The cover member 44 can be secured to the body member 42 in any suitable manner such as, for example, mechanical fasteners. The lower joint members 46A, 46B are removably secured to the bottom of the body member 42 at ends of the body member 42. The illustrated lower joint members 46A, 46B are removably secured to body member 42 in any suitable manner for attachment and removal of the side portions 16A, 16B to the base portion 16. The lower joint members 46A, 46B perpendicularly extend from the ends of the body member 42 at the bottom and each has an upward facing surface with a groove 48 formed therein for receiving a lower end of a lower pivot pin to secure the side portion 18A, 18B to the base portion 16 in a pivoting manor. The groove 48 defines the path of movement of the side portion 18A, 18B relative the base portion 16. The illustrated groove 48 is arcuate so that the side portion 16A, 16B moves along an arcuate path relative to the base portion 16. The illustrated body member 42 also has integral upper joint members 50A, 50B perpendicularly extending from the ends of the body member 42 at the top and each has a downward facing surface with groove 48 formed therein for receiving an upper end of an upper pivot pin to secure the side portion 18A, 18B to the base portion 16 in a pivoting manor. The illustrated grooves 48 in the upper joint members 50A, 50B are arcuate and mirror the grooves 48 in the lower joint members 46A, 46B. The pivot pins are preferably provided with resilient spring members to bias the side portions 18A, 18B inward and in contact with the sides of the user's neck 14. The spring members can be of any suitable type. It is noted that the joints between the base portion 16 and the side portions 18A, 18B can alternatively be of any other suitable type. It is also noted that the base portion 16 can have any other suitable configuration.

The illustrated components 42, 44, 46 of the base portion 16 are molded of a suitable plastic material. It is noted however, that the illustrated components 42, 44, 46 of the base portion 16 can alternatively comprise any other suitable material and can alternatively be manufactured in any other suitable manner.

Figure 11:
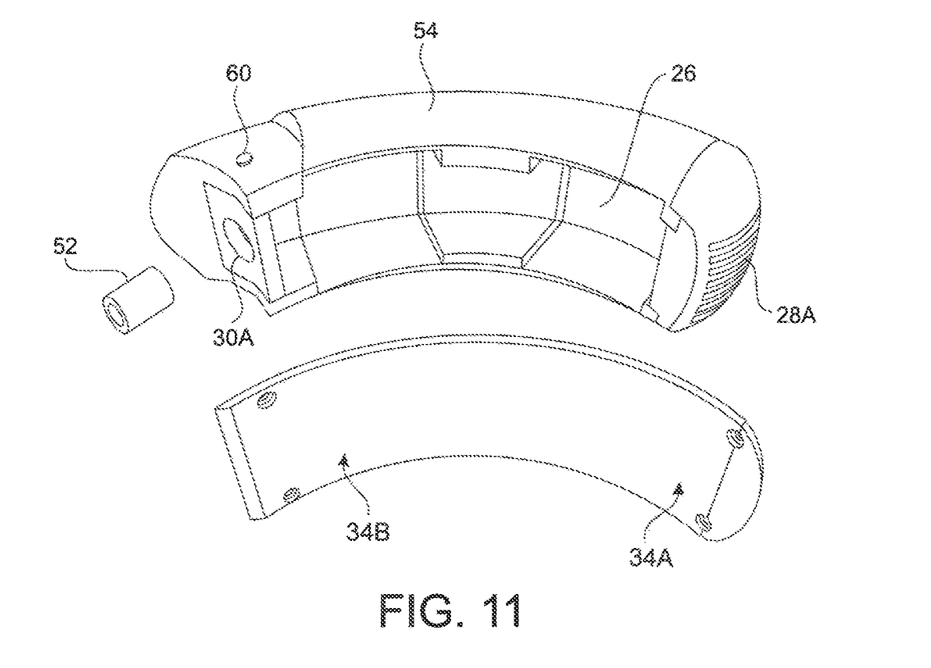
FIG. 11 is an exploded view of the left-side portion of the personal temperature regulating device of FIGS. 1 to 8, wherein internal component are eliminated for clarity.
Figure 12:
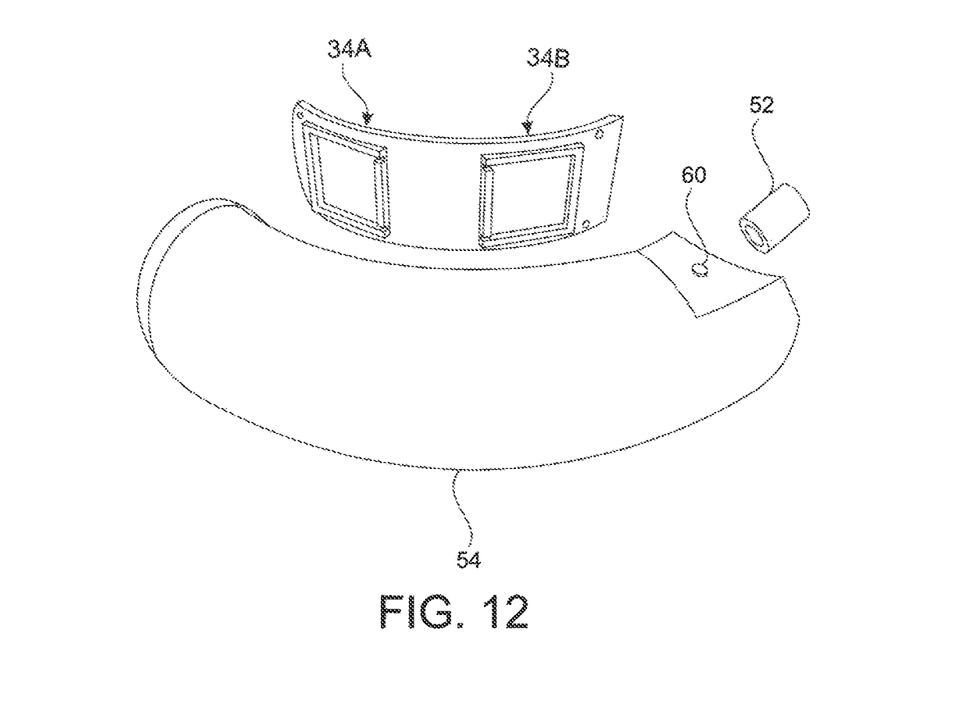
FIG. 12 is another exploded view of the left-side portion of FIG. 11.

As best shown in FIGS. 11 and 12, the illustrated left side portion 16A of the housing 12 is generally arcuate shaped so that it extends about the left side portion of the user's neck 14. It is noted that the right-side portion 18B is a mirror image of the left side portion 16A and thus will not be separately described in detail herein. The side portion 16A forms the hollow interior space or air duct 26. The illustrated air duct 26 has an air inlet 28A at the forward end of the side portion 18A. The illustrated air inlet 28A has a plurality of vertically spaced apart and horizontally extending slots or openings extending through the wall but any other suitable configuration can be utilized. The illustrated air duct 26 also has an air outlet 30A in the rear end of the side portion 18A. The air outlet 30A is associated with one of the air inlets 22A of the base portion 16. The illustrated air outlet 30A is a circular opening extending through the wall but any other suitable configuration can be utilized. The illustrated air outlet 30A is in communication with the air inlet 22A of the base portion 16 with a flexible tube or hose 52 extending therebetween. The flexible tube 52 can be food safe pliable tubing or the like. It is noted however, that the inlet 22A and the outlet 30A can alternatively be communicated in any other suitable manner.

The illustrated side portion 18A includes a body member 54 that primarily forms the top, bottom, front, rear, and outer walls of the side portion 18A, and cold space members 34A, 34B that form the inner wall as an integral one piece member. The illustrated cold space members 34A, 34B are removably secured to the body member 54 in any suitable manner for assembly and repair of components located within the side portion 18A of the housing 12. The cold space members 34A, 34B can be secured to the body member 54 in any suitable manner such as, for example, mechanical fasteners. The illustrated cold space members 34A, 34B close the open inner side of the body member 54. The illustrated cold space members 34A, 34B have an outer side surface 56A, 56B that is arcuate and configured to face and thermally contact the side of the user's neck 14. The illustrated cold space members have an inner side surface 58A, 58B that is within the air duct 26 and configured to thermally contact the thermoelectric devices 32A, 32B therein. The illustrated inner side surfaces 58A, 58B each have a recess for receiving the associated thermoelectric module 32A, 32B. It is noted that while the illustrated cold space members 34A, 34B are integrated as a single component, they can alternatively be formed as separate components. The illustrated body member 54 also has an upward facing surface at the top of the rearward end of the body member 54 and a downward facing surface at the bottom of the rearward end of the body member 54. Each of these surfaces is provided with a pin opening 60 for the joint with the base portion 16. The upper pin opening 16 receives the lower end of the upper pivot pin while the lower pin opening receives the upper end of the lower pivot pin so that the side portion 18A can pivot relative to the base portion 16. It is also noted that the side portion 16A can have any other suitable configuration.

The illustrated body member 564 of the side portion 16A is molded of a suitable plastic material. It is noted however, that the body member 54 of the side portion 16A can alternatively comprise any other suitable material and can be manufactured in any other suitable manner. The illustrated cold space members 34A, 34B comprises aluminum or the like. It is noted however, that the cold space members 34A, 34B can alternatively comprise any other suitable material.

The illustrated personal temperature regulating device 10 includes a total of four of the thermoelectric devices 32A, 32B, 32C, 32D where two of the thermoelectric devices 32A, 32B are located on the left side portion 18A, and two of the thermoelectric devices 32C, 32D are located on the right side portion 18B. This configuration enables only the side portions 18A, 18b to selectively heat and cool the user's neck 14. That is, the base portion 16 does not heat and/or cool the back or base of the user's neck 14, and the front of the user's neck 14 is also not cooled or heated. The cooling and/or heating is thus only applied near the pulse points on the user's neck 14 to more rapidly lower or raise the user's core body temperate without giving a false sense of temperature change. As best shown in FIG. 9, the illustrated thermoelectric devices 32A, 32B, 32C, 32D are located near the carotid arteries 62A, 62B and the vertebral arteries 64A, 64B on each side of the user's neck 14. It is noted, however, that any other suitable quantity of thermoelectric devices 32A, 32B, 32C, 32D and/or locations of the thermoelectric devices 32A, 32B, 32C, 32D can alternatively be utilized.

The illustrated thermoelectric devices 32A, 32B, 32C, 32D are each a semiconductor-based Peltier-type thermoelectric cooler such that heat is moved from one side to the other when low voltage direct current is applied. The illustrated thermoelectric cooler includes a thermoelectric module 66A, 66B, 66C, 66D, a heat sink 36A, 36B, 36C, 36D, and one of the cold space members 34A, 34B, 34C, 34D. The illustrated thermoelectric module 66a, 66B, 66C, 66D can includes pairs of P-type and N-type semiconductor thermo elements to form a thermocouple which are electrically coupled in series and thermally connected in parallel. This type of thermoelectric module 66a, 66B, 66C, 66D is considered to be highly reliable due to its solid state construction. When direct current power is supplied to the thermoelectric module 66a, 66B, 66C, 66D, heat is pumped from a first or cold side to an opposed second or hot side. The illustrated thermoelectric module 66a, 66B, 66C, 66D comprises bismuth telluride but any other suitable material or materials can alternatively be utilized. It is noted that the thermoelectric devices 32A, 32B, 32C, 32D can alternatively be of any other suitable type.

The illustrated heat sink 36A, 36B, 36C, 36D is in thermal transfer contact with the hot side of the thermoelectric module 66A, 66B, 66C, 66D (when cooling) in order to expedite the transfer of heat away from the hot side of the thermoelectric module 66A, 66B, 66C, 66D. The illustrated heat sink 36A, 36B, 36C, 36D comprises aluminum but any other suitable material or materials can alternatively be utilized. The illustrated heat sink 36A, 36B, 36C, 36D is also of the finned type but can alternatively be of any other suitable type. The illustrated electric fans 38A, 38B blow air over the cooling fins of the heat sink 36A, 36B, 36C, 36D to expedite heat transfer therebetween.

The illustrated cold space member 34A, 34B, 3C, 34D is in thermal transfer contact with the cold side of the thermoelectric module 66A, 66B, 66C, 66D in order to expedite the absorption of heat by the cold side of the thermoelectric module 66A, 66B, 66C, 66D. The illustrated cold space member 34A, 34B, 3C, 34D comprises aluminum but any other suitable material or materials can alternatively be utilized. The cold space member 34A, 34B, 3C, 34D can alternatively be of any other suitable type.

The illustrated personal temperature regulating device 10 includes a total of two of the electric fans 38A, 38B with each one of the electric fans 38A, 38B located at a separate one of the two laterally spaced apart air outlets 24a, 24B located at the back of the air duct 20 in the base portion 16. It is noted however, that any other suitable quantity of electric fans 38A, 38B and/or locations of the electric fans 38A, 38B can alternatively be utilized. Mounted in this location, when powered, the electric fans 38A, 38B pull air into the two air duct inlets 28A, 28B at the front of the side portions 18A, 18B, rearwardly through the air ducts 26 and over the heat sinks 36A, 36B, 36C, 36D of the thermoelectric modules 32A, 32B, 32C, 32D located within the air ducts 26, rearwardly out of the air duct outlets 30A, 30B at the rear of the side portions 18A, 18B and into the air duct inlets 22A, 22B at the front of the base portion 18 through the connecting tubes 52, and rearwardly out of the air duct outlets 24A, 24B at the rear of the base portion 16 via the electric fans 38A, 38B. That is, the illustrated electric fans 38a, 38B generally provide two straight and parallel flow paths rearwardly through the device 10. It is noted however, that because the illustrated air duct 20 is open within the base portion 18 between the inlets 22A, 22B and the outlets 24A, 24B, there can be some mixing within the air duct 20 of the base portion 16. It is also noted that the air duct 20 within the base portion 16 can alternatively be divided into two parts in order to prevent such mixing if desired but the open design is preferred so that air flow continues along both paths even upon failure of one of the electric fans 38A, 38B. It is further noted that the electric fans 38A, 38B can be of any suitable type to provide suitable air flow through the illustrated personal temperature regulating device 10.

Figure 13:
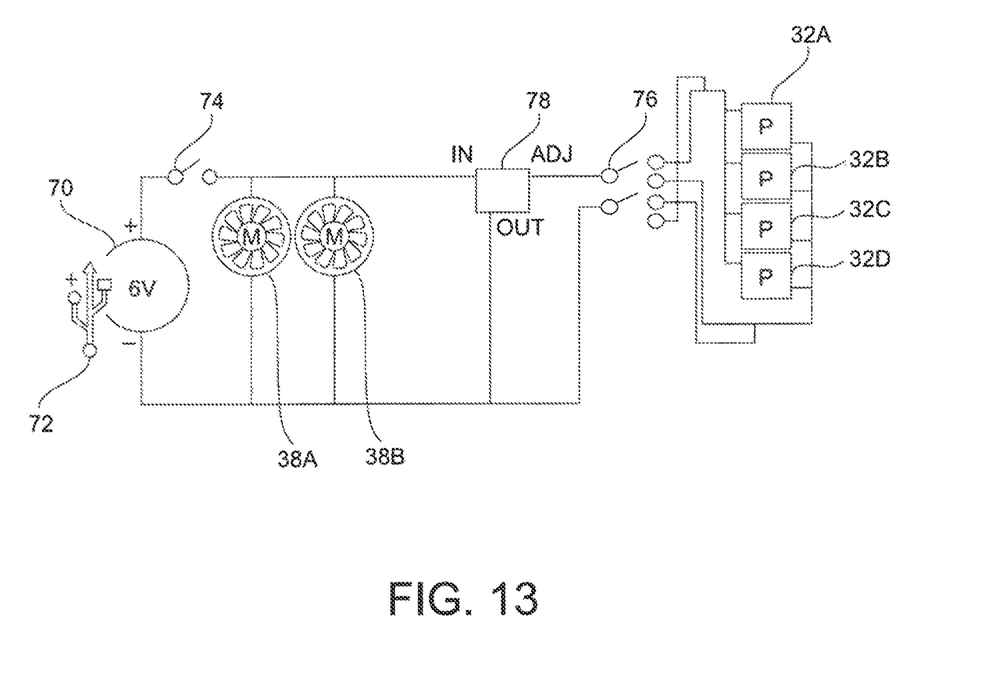
FIG. 13 is an electrical schematic of the personal temperature regulating device of FIGS. 1 to 8.

FIG. 13 shows an exemplary electrical schematic for the personal temperature regulating device 10. A DC electric power source 70 selectively provides electric power to the electric fans 38A, 38B in the base portion 16 and the thermoelectric modules 32A, 32B, 32C, 32D in the side portions 18A, 18B. The DC electric power source 70 can be in the form of rechargeable battery packs located within the air duct 20 of the base portion 16 between the electric fans 38A, 38B or any other suitable location. The illustrated personal temperature regulating device 10 includes a USB charging port 72 for charging the rechargeable battery packs. It is noted that an external electric power source can alternatively be utilized. An on/off or first switch 74 is provided to selectively cut off or provide power to the electric fans 38A, 38B in the base portion 16 and the thermoelectric modules 32A, 32B, 32C, 32D in the side portions 18A, 18B. The on/off switch 74 can be any suitable type of electric switch. The illustrated on/off switch 74 is provided in the first or upper switch opening 40A at the rear of the base portion 18 but any other suitable location can alternatively be utilized. A cool/heat or second switch 76 is provided to selectively change the polarity of the thermoelectric modules 32A, 32B, 32C, 32D in the side portions 18A, 18B so that they either cool or heat the cold space members 34A, 32B, 32C, 32D. The cool/heat switch 76 can be any suitable type of electric switch such as, for example, single pull double throw (SPDT) switch. The illustrated cool/heat switch 76 is provided in the second or lower switch opening 40B at the rear of the base portion 18 but any other suitable location can alternatively be utilized. The illustrated personal temperature regulating device 10 also includes a current limiter 78 which ensures that the thermoelectric devices 2A, 32B, 32C, 32D do not become too cold or too hot. It is noted that the electrical circuit can alternatively include other features such as, for example, indicator lights for one or both of the switches, a potentiometer for adjusting the temperature of the thermoelectric devices, and/or the like. It is also noted that the personal temperature regulating device 10 can alternatively have any other suitable electrical circuit configuration.

For use in lowering body temperature, the user first selects cooling with the cool/heat switch 76 and actives the device 10 with the on/off switch 74. The user then outwardly pivots the side portions 18A, 18B relative to base portion 16 to widen the front opening 80 between the front ends of the side portions 18A, 18B so that the user's neck 14 can be placed therethrough so that the base portion 16 is adjacent the base of the user's neck 14 and the side portions 18A, 18B engage the lateral sides of the user's neck 14. The spring loaded pivots ensure that the cold space members 34A, 34B, 34C, 34D of the side portions 18A, 18B remain engaged with the sides of the user's neck 14. Heat is pumped from the first or cold side of the thermoelectric devices 32A, 32B, 32C, 32D in heat transfer communication with the cold space members 4A, 34B, 34C, 34D to an opposed second or hot side of the thermoelectric devices 32A, 32B, 32C, 32D in heat transfer communication with the heat sinks 36A, 36B, 36C, 36D. The cooling air, drawn by the electric fans 38A, 38B, flow over the heat sinks 36A, 36B, 36C, 36D to remove heat from the heat sinks 36A, 36B, 36C, 36D and eject the heat rearwardly out the rear of the base portion 16. As a result, heat is drawn from the user's neck 14 near the carotid arteries 62A, 62B and the vertebral arteries 64A, 64B to rapidly lower the body temperature of the user. For use in raising body temperature, the user first selects heating with the cool/heat switch 76 and the remainder is the same except that the flow of heat is in the reverse direction.

It is noted that each of the features of the various disclosed embodiments of the present invention can be utilized in any combination with each of the other disclosed embodiments of the present invention.

From the above disclosure it can be appreciated that the personal temperature regulating devices 10 according to the present invention are self-contained devices that rapidly lower and/or raise the user's body temperature.

The preferred embodiments of this invention can be achieved by many techniques and methods known to persons who are skilled in this field. To those skilled and knowledgeable in the arts to which the present invention pertains, many widely differing embodiments will be suggested by the foregoing without departing from the intent and scope of the present invention. The descriptions and disclosures herein are intended solely for purposes of illustration and should not be construed as limiting the scope of the present invention.

What is claimed is:

1. A body temperature regulating device for use on a body portion of a user, the temperature regulating device comprising:
   a housing configured to extend partially about the body portion and having a base portion, a first side portion extending from a first end of the base portion, and a second side portion extending from a second end of the base portion opposite the first, end;
   wherein the base portion has an interior air duct with a first air inlet, a second air inlet, and at least one air outlet;
   wherein the first side portion has a distal end opposite the base portion, a proximal end at the base portion, and an interior air duct extending from an air inlet at the distal end to an air outlet at the proximal end in communication with the first air inlet of the interior air duct of the base portion;

wherein the second side portion has a distal end opposite the base portion, a proximal end at the base portion, and an interior air duct extending from an air inlet at the distal end to an air outlet at the proximal end in communication with the second air inlet of the interior air duct of the base portion;

at least one thermoelectric device located within the first side portion and having a first side in thermal connection with a cold space member at least partially forming an exterior side of the first side portion and a second side in thermal connection with a heat sink located within the air duct of the first side portion;

at least one thermoelectric device located within the second side portion and having a first side in thermal connection with a cold space member at least partially forming an exterior side of the second side portion and a second side in thermal connection with a heat sink located within the air duct of the second side portion; and at least one fan within the air duct of the base portion at the at least one air outlet of the base, portion and configured to pull air into at least one of the air inlets of the first and second side portions and out through the at least one air outlet of the base portion.

2. The body temperature regulating device of claim 1, wherein the housing configured to extend partially about a neck of the user.

3. The body temperature regulating device of claim 1, wherein the at least one air outlet comprises two air outlets, and the at least one fan comprises two fans with each of the fans at a different one of the air outlets.

4. The body temperature, regulating device of claim 3, wherein the at least one thermoelectric device located within the first side portion comprises two thermoelectric devices located within the first side portion, and wherein the at least one thermoelectric device located within the second side portion comprises two thermoelectric devices located within the second side portion.

5. The body temperature regulating device of claim 1, wherein the at least one thermoelectric device located within the first side portion comprises two thermoelectric devices located within the first side portion, and wherein the at least one thermoelectric device located within the second side portion comprises two thermoelectric devices located within the second side portion.

6. The body temperature regulating device of claim 1, wherein the thermoelectric devices are configured to selectively heat and cool the body part.

7. The body temperature regulating device of claim 6, wherein only the side portions of the housing selectively heat and cool the body part.

8. The body temperature regulating device of claim 6, wherein base portion of the housing does not heat and cool the body part.

9. A body temperature regulating device for use on opposite sides of a body portion of a user, the temperature regulating device comprising:

a housing having an arcuate-shaped base portion; an arcuate-shaped first side portion extending from a first end of the base portion, and an arcuate-shaped second side portion extending from a second end of the base portion opposite the first end, and configured to partially encircle the body portion of the user with the first and second side portions of the housing located at the opposite sides of the body portion of the user;

first and second thermoelectric devices located within the first side portion and each having a first side in thermal connection with a first cold space member at least partially forming an exterior side of the first side portion and a second side in thermal connection with a heat sink located within an air duct of the first side portion;

first and second thermoelectric devices located within the second side portion and each having a first side in thermal connection with a second cold space member at least partially forming an exterior side of the second side portion and a second side in thermal connection with a heat sink located within the air duct of the second side portion;

wherein the first and second thermoelectric devices located in the first side portion and the first and second thermoelectric devices located in the second side portion are configured to be located at the opposite sides of the body part of the user; and further comprising at least one fan configured to pull air through the air dug in the first and second side portions;

wherein the at least one fan is located in the base portion of the housing.

10. The body temperature regulating device of claim 9, wherein housing configured to extend partially about a neck of the user.

11. The body temperature regulating device of claim 9, wherein the thermoelectric devices are configured to selectively heat and cool the body part.

12. The body temperature regulating device oaf claim 11, wherein the housing is configured so that only the side portions of the housing selectively heat and cool the body part.

13. The body temperature regulating device of claim 11, wherein the housing is configured so that base portion of the housing does not heat and cool the body part.

14. The body temperature regulating device of claim 9, wherein the at least one fan comprises two fans.

15. A body temperature regulating device for use on a neck of a user, the temperature regulating device comprising:

a housing configured to extend partially about the neck of the user and having a base portion, a first side portion extending from a first end of the base portion, and a second side portion extending from a second end of the base portion opposite the first end;

wherein the base portion has an interior air duct with a first air inlet, a second air inlet, a first sir outlet, and a second air outlet;

wherein the first side portion has a distal end opposite the base portion, a proximal end at the base portion, and an interior air duct extending from an air inlet at the distal end to an air outlet at the proximal end in communication with the first air inlet of the interior air duct of the base portion;

wherein the second side portion has a distal end opposite the base portion, a proximal end at the base portion, and an interior air duct extending from an air inlet at the distal end to an air outlet at the proximal end in communication with the second air inlet of the interior air duct of the base portion;

two thermoelectric devices located within the first side portion and each having a first side in thermal connection with a cold space member t least partially forming an exterior side of the first side portion and a second side in thermal connection with a heat sink located within the air duct of the first side portion;

two thermoelectric devices located within the second side portion and each having a first side in thermal connection with a cold space member at least partially forming an exterior side of the second side portion and a second side in thermal connection with a heat sink located within the air duct of the second side portion;

a first fan within the air duct of the base portion at the first air outlet of the base portion and configured to pull air into at least one of the air inlets of the first and second side portions and out through the first air outlet of the base portion; and a second fan within the air duct of the base portion at the second air outlet of the base portion and configured to pull air into at least one of the air inlets of the first and second side portions and out through the second air outlet of the base portion.

16. The body temperature regulating device of claim 15, wherein the thermoelectric devices are configured to selectively heat and cool the neck.

17. The body temperature regulating device of claim 16, wherein only the side portions of the housing selectively heat and cool the neck.

18. The body temperature regulating device of claim 16, herein the base portion of the housing does hot heat and cool the neck.

* * * * *